US009579236B2

(12) United States Patent
Amedi et al.

(10) Patent No.: US 9,579,236 B2
(45) Date of Patent: Feb. 28, 2017

(54) REPRESENTING VISUAL IMAGES BY ALTERNATIVE SENSES (75) Inventors: Amir Amedi, Jerusalem (IL); Shlomo Hanassy, Ashod (IL)

(73) Assignee: Yissum Research Development Company of The Hebrew University of Jerusalem LTD., Jerusalem (IL)

(*) Notice: Subject to any disclaimer, the term of this patent is extended or adjusted under 35 U.S.C. 154(b) by 260 days.

(21) Appl. No.: 13/505,642

(22) PCT Filed: Nov. 3, 2010

(86) PCT No.: PCT/IB2010/054975
§ 371 (c)(1),
(2), (4) Date: May 14, 2012

(87) PCT Pub. No.: WO2011/055309
PCT Pub. Date: May 12, 2011

(65) Prior Publication Data
US 2013/0194402 A1 Aug. 1, 2013

Related U.S. Application Data (60) Provisional application No. 61/257,475, filed on Nov. 3, 2009.

(51) Int. Cl.
*H04N 9/47* (2006.01)
*H04N 7/18* (2006.01)
(Continued)

(52) U.S. Cl.
CPC .............. *A61F 9/08* (2013.01); *A61H 3/061* (2013.01); *G09B 21/003* (2013.01); *G09B 21/006* (2013.01); *G09B 21/007* (2013.01)

(58) Field of Classification Search
CPC ........ A61F 9/08; G09B 21/003; G09B 21/006
(Continued)

(56) References Cited

U.S. PATENT DOCUMENTS 6,963,656 B1 * 11/2005 Persaud ............... G09B 21/006
348/62
7,308,314 B2 * 12/2007 Havey ................ A61N 1/36046
607/54
2011/0216179 A1 * 9/2011 Dialameh ......... G06F 17/30247
348/62

FOREIGN PATENT DOCUMENTS

EP 0410045 1/1991
WO 9958087 11/1999
WO 2007105927 9/2007

OTHER PUBLICATIONS

International Search Report for PCT application No. PCT/IB2010/054975 issued by the ISA/EPO dated Apr. 20, 2011.
(Continued)

*Primary Examiner* — Chikaodili E Anyikire
(74) *Attorney, Agent, or Firm* — Pearl Cohen Zedek Latzer Baratz LLP (57) ABSTRACT A method of representing visual images by alternative senses is provided herein. The method includes the following stages: obtaining an image of an environment having a background and physical objects distinguishable from the background; slicing the image into a plurality of slices; identifying, for each slice at a time, and slice by slice in a specified order, if at least a portion of the physical objects being contained within the slice; applying, in the specified order, a conversion function to each identified portion of the physical objects for generating a sound or tactile object-dependent signal; associating a sound or tactile location-dependent signal unique for each slice; superpositioning, in the specified order, each object-dependent signal with a respective location-dependent signal for creating a combined object-location signal; and outputting the combined object-location signal to a user via an interface in a form usable for a blind or visually impaired person.

16 Claims, 7 Drawing Sheets (51) Int. Cl.
*A61F 9/08* (2006.01)
*A61H 3/06* (2006.01)
*G09B 21/00* (2006.01)

(58) Field of Classification Search
USPC .......................................................... 348/62
See application file for complete search history.

(56) References Cited

OTHER PUBLICATIONS

Written Opinion for PCT application No. PCT/IB2010/054975 issued by the ISA/EPO dated Apr. 20, 2011.

* cited by examiner

REPRESENTING VISUAL IMAGES BY ALTERNATIVE SENSES

CROSS-REFERENCE TO RELATED APPLICATIONS

This application is a National Phase Application of PCT International Application No. PCT/IB2010/054975, International Filing Date Nov. 3, 2010, entitled: "REPRESENTING VISUAL IMAGES BY ALTERNATIVE SENSES", published on May 12, 2011 as International Patent Application Publication No. WO 2011/055309, claiming the benefit of US Provisional Patent Application No. 61/257,475, filed Nov. 3, 2009, all of which are hereby incorporated by reference in their entirety.

BACKGROUND

1. Technical Field

The present invention relates to the field of vision aids and more particularly, to vision aids based on image-to-sound and image-to-touch conversions.

2. Discussion of the Related Art

Blind and visually impaired persons face daily challenges of mobility and orientation that severely affect their well being. With the technological development of information technology, modern lifestyle involves extended use of computers that usually necessitate interfacing using a graphic display.

According to some scientific studies, blind and visually impaired persons tend to develop enhanced hearing. Specifically, people who have been blind from an early age are better at locating sound sources than sighted persons and have better tactile abilities (e.g. reading Braille). Furthermore, brain scans suggest that parts of the brain normally used in processing sight, such as the visual cortex, may be converted to enhancing a blind person's ability to process sound and touch.

Therefore, there have been some attempts in representing vision by converting images taken from a live camera into sound signals. One example is the vOICe vision technology that offers blind persons an experience of live camera views through image-to-sound renderings.

Another example is the BrainPort® technology that has been developed for use as a visual aid. The BrainPort® technology has demonstrated its ability to allow a blind person to see his surroundings in polygonal and pixel form. In this scenario, a camera picks up the image of the surrounding; the information is processed by a chip which converts it into impulses which are sent through an electrode array, via the tongue, to the person's brain.

Theoretically, the use of digital senses could lead to synthetic vision with truly visual orientation through cross-modal sensory integration, by exploiting the existing multi-sensory processing and neural plasticity of the human brain through training and education.

BRIEF SUMMARY

One aspect of the invention provides a method that includes the following stages: obtaining, using an imaging device, an image of an environment having a background and at least one physical object distinguishable from the background; slicing the image into a plurality of slices; identifying, for each slice at a time, and slice by slice in a specified order, if at least a portion of the at least one physical object being contained within the slice; applying, in the specified order, a conversion function to each identified portion of the at least one physical object for generating a sound or tactile object-dependent signal; associating a sound or tactile location-dependent signal unique for each slice; superpositioning, in the specified order, each object-dependent signal with a respective location-dependent signal for creating a combined object-location signal; and outputting the combined object-location signal to a user via an interface, wherein the combined object-location signal being usable for a blind person to determine location and characteristics of the at least one physical object in relation to the environment.

Another aspect of the invention provides a method that includes: obtaining, using an imaging device, a three-dimensional model of an environment containing at least one physical object; partitioning the three-dimensional model by surfaces; identifying, for each surface at a time, and surface by surface in a specified order, if at least a portion of the at least one physical object being cross-sectioned by the surface; applying, in the specified order, a conversion function to each identified cross-section of the at least one physical object for generating a sound or tactile object-dependent signal; associating a sound or tactile location-dependent signal unique for each surface; superpositioning, in the specified order, each object-dependent signal with a respective location-dependent signal for creating a combined object-location signal; and outputting the combined object-location signal to a user via an interface, wherein the combined object-location signal being usable for a blind person to determine location and characteristics of the at least one physical object in relation to the environment.

Yet another aspect of the invention provides a method comprising: slicing a graphic display into a plurality of slices, wherein the graphic display exhibits a plurality of objects and icons that are associated each with a specified appearance and a specified functionality; applying, for each slice, a conversion function to each object or icon contained within the slice, for generating a sound or tactile object-dependent signal; associating a sound or tactile location-dependent signal unique for each slice; tracking a user-controlled indicator over the graphic display for detecting a location of the indicator; superpositioning, over time, the location-dependent signal associated with the location of the indicator with all object-dependent signals of the objects or icon that are located within a specified range from the indicator, for creating a combined object-location signal; and outputting the combined object-location signal to a user via an interface, wherein the combined object-location signal being usable for a blind person to determine location, appearance, functionality of objects and icons on the graphic display, wherein at least of the obtaining, the slicing, the tracking, the applying, the associating, the superpositioning, and the outputting is performed by at least one computer.

These, additional, and/or other aspects and/or advantages of the present invention are: set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

The drawings together with the following detailed description make apparent to those skilled in the art how the invention may be embodied in practice.

DETAILED DESCRIPTION

Prior to setting forth the detailed description, it may be helpful to set forth definitions of certain terms that will be used hereinafter.

The term "physical object" as used herein in this application refers to any entity that has both spatial and temporal existence. Additionally, for the purposes of this application, physical objects include any entity whose geometric characteristics including texture, shape, color, and movement may be detected by at least one specified imaging device.

The term "imaging device" as used herein in this application, is broadly defined as any device that captures physical objects and represents them as an image. Imaging devices may be optic based, but may also include Radio Frequency (RF) imaging, Ultra Sound (US) imaging, Infra Red (IF) imaging and the like. Thus, an imaging device may function in limited lighting conditions.

The term "icon" or "computer icon" as used herein in this application in the context of a graphic computer display is a small pictogram. Icons have been used to supplement the normal alphanumeric of the computer. Modern computers now can handle bitmapped graphics on the display terminal, so the icons are widely used to assist users. In this application, icons are broadly defined to include any graphical entity presented over a computer display that has some specified functionality.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figure 1:
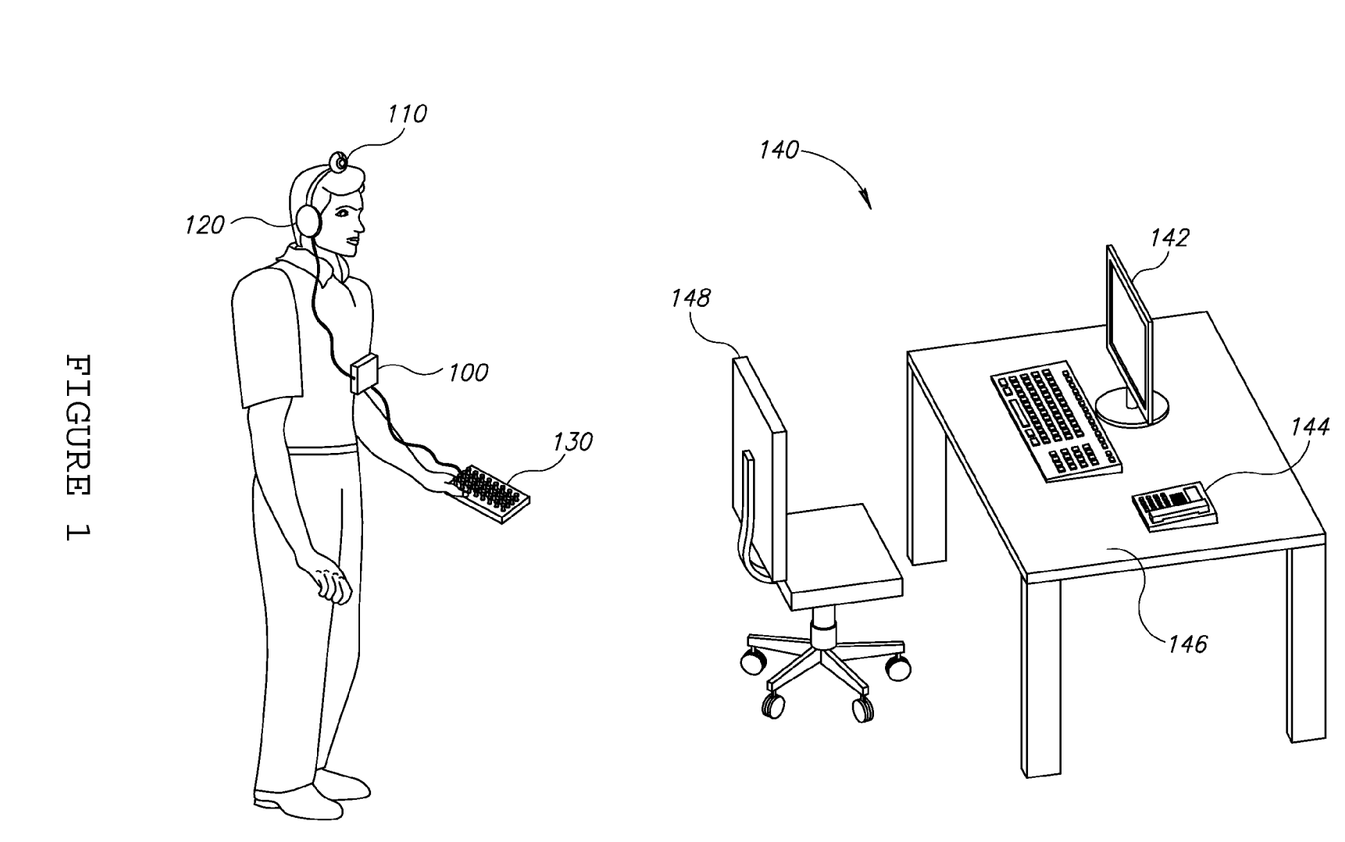
FIG. 1 is a high level schematic diagram illustrating a system according to some embodiments of the invention.

FIG. 1 is a high level schematic diagram illustrating a system according to some embodiments of the invention. The system includes: an imaging device 110; a data processing module 100; headphones 120; and a tactile interface 130. As shown. the system may be easily mounted on a user, with imaging device 110 being placed on top of the user's head, data processing module 100 connected via a cable to both headphones 120, imaging device 110, and tactile interface 130. Tactile interface 130 may be implemented as a pins matrix having an array of pins, (e.g., sixty by forty pins) that are responsive to a signal from data processing module 100 such that each pin is positioned in a specified height. The user is facing a specific environment 140 that may include, for example, a desk 146, a chair 148, a computer screen 142, and a phone 144.

Data processing module 100, may be in the form of a computer that includes, in some embodiments, a processor (not shown) and a storage module (not shown). Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files. Storage modules suitable for tangibly embodying computer program instructions and data include all forms of non-volatile memory, including by way of example semiconductor memory devices, such as EPROM, EEPROM, and flash memory devices and also magneto-optic storage devices. Exemplary data processing modules 100 may include cellular communication devices such as cellular phone, Personal Device Accessories (PDAs) and the like.

Figure 2:
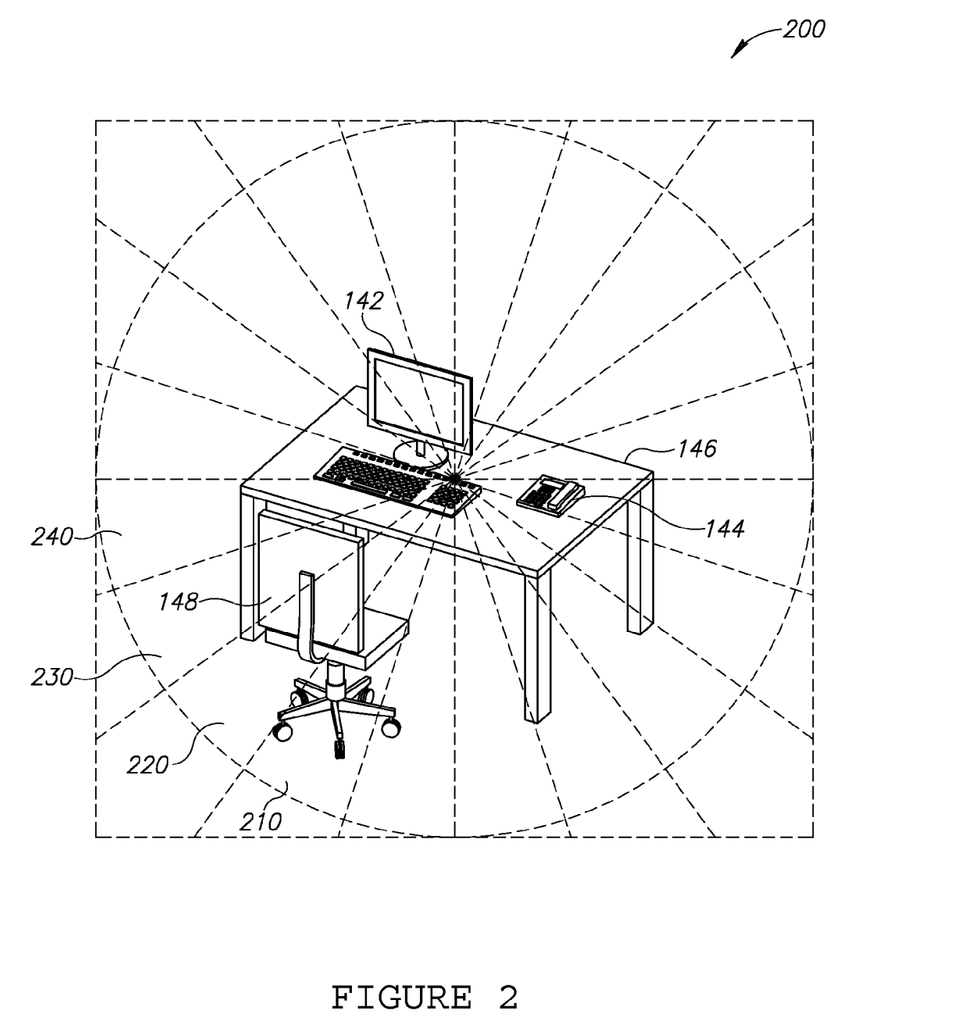
FIG. 2 is an image diagram illustrating an aspect according to some embodiments of the invention.

FIG. 2 is an image diagram captured by imaging device 110 and illustrating an aspect according to some embodiments of the invention. In operation, imaging device 110 is configured to obtain an image 200 of environment 140, including the physical objects within it. Thus, desk 146, chair 148, computer screen 142, and phone 144 are all contained within image 200.

Data processing module 100 is configured to: slice image 200 into a plurality of slices, such as 210, 220, 230 and 240; identify, for each slice at a time, and slice by slice in a specified order (e.g., 240, 230, 220 and finally 210), if at least a portion of the at least one physical object being contained within the slice; apply, in the specified order, a conversion function to each identified portion of the at least one physical object for generating a sound or tactile object-dependent signal; associate a sound or tactile location-dependent signal unique for each slice; superposition, in the specified order, each object-dependent signal with a respective location-dependent signal for creating a combined object-location signal; and output the combined object-location signal to a user via user interfaces 120 and 130. Specifically, the combined object-location signal is being presented in a format that may be usable for a blind or visually impaired person to determine location and characteristics of the at least one physical object in relation to the environment.

Consistent with some embodiments of the invention, the conversion function may map any characteristic of an object, such as shape, color, position in a scene into a corresponding set of sounds, such that a blind person may be trained to associate any of the specified sounds with a respective characteristic of the object in the scene.

During experimentations, the applicants have discovered that a mapping of objects characteristics into a corresponding combination of real musical instruments yields significantly better results in carrying out embodiments of the present invention than any other set of sounds that have been tested. The better results were in terms of several aspects. According to one aspect, the musical instrument mapping has shortened the training time required for a blind person to study the object-to-sound mapping. According to another aspect, the musical instruments mapping has provided higher sound resolution being the ability to describe in sound a given visual scene. According to yet another aspect, the musical instruments mapping results in a higher sensual stimulation saturation point being a point in which a blind person becomes overwhelmed by too much sound information for a given scene, beyond interpretation ability.

From a technical point of view, carrying out the aforementioned musical instruments mapping may be by presampling different types of real musical instruments and playing them in accordance with the object-to-sound mapping. Such a mapping may result, for example, in a musical chord for a specified shape and a musical scale for variation in elevation over the horizon. Similarly, different types of musical instruments may be used to represent different elevations of objects in the scene (or any other position) and different colors of the objects in the scene.

Referring back to FIG. 2, image 200 comprises an array of pixels (not shown), each pixel being associated with a location, a color and a brightness level. The conversion function may be any specified image-to-sound algorithm or image-to-touch algorithm that maps a two dimensional image into a temporal sound signal or two dimensional tactile signal in accordance with the location, the color and the brightness level of each pixel.

According to some embodiments of the invention, data processing module 100 being further configured to slice a circular portion of the image, wherein each slice being a circular sector, and wherein the specified order being clockwise or counterclockwise. The width of the circular sector may be selected in view of the resolution required in the slicing. Specifically, the width may be affected by the amount and complexity of the physical objects on image 200.

According to other embodiments of the invention, data processing module 100 being further configured to slice a circular portion of the image, wherein each slice being a circular ring having a width defined by an inner radius and an outer radius, and wherein the specified order being radially inward or radially outward. The width of the ring may be selected in view of the resolution required in the slicing. Specifically, the width may be affected by the amount and complexity of the physical objects on image 200.

Advantageously, using a circular configuration and circular sectors or circular rings as slices is compliant with the eye-brain physiology so that improved results may be achieved using the circular configuration. This organization is a transformation from Euclidian image on the retina into an eccentricity and polar angle coordinates system in the cerebral cortex. This is achieved by simulating a rotating wedge in which a larger representation is given to the fovea, the center of the visual field (i.e. polar angle eccentricity representation with magnification factor). This scanning method is then transformed and maintained in the auditory spectrum using at least some embodiments of the invention.

Figure 3:
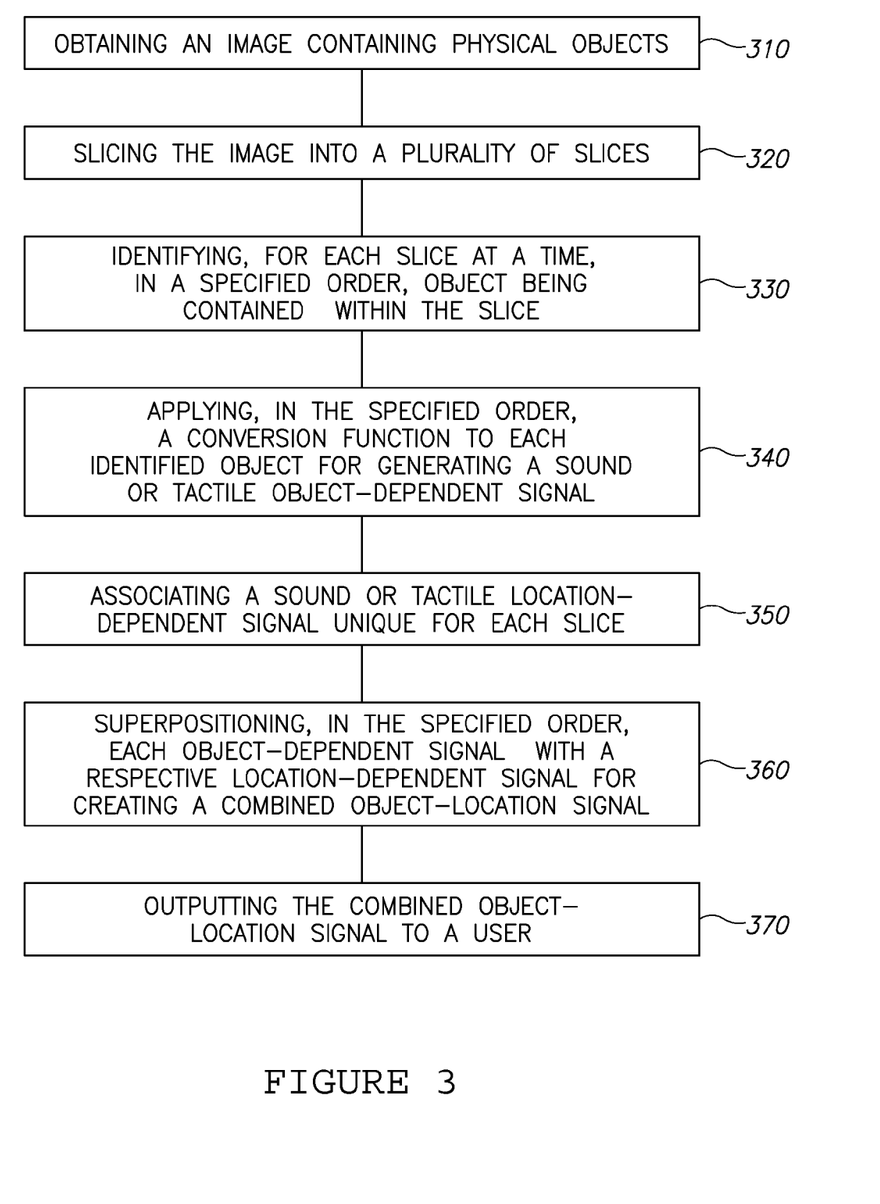
FIG. 3 is a high level flowchart illustrating a method according to some embodiments of the invention.

FIG. 3 is a high level flowchart illustrating a method according to some embodiments of the invention. The method includes obtaining, using an imaging device, an image of an environment having a background and at least one physical object distinguishable from the background 310; slicing the image into a plurality of slices 320; identifying, for each slice at a time, and slice by slice in a specified order, if at least a portion of the at least one physical object being contained within the slice 330; applying, in the specified order, a conversion function to each identified portion of the at least one physical object for generating a sound or tactile object-dependent signal 340; associating a sound or tactile location-dependent signal unique for each slice 350; superpositioning, in the specified order, each object-dependent signal with a respective location-dependent signal for creating a combined object-location signal 360; and outputting the combined object-location signal to a user via an interface 370, wherein the combined object-location signal being usable for a blind person to determine location and characteristics of the at least one physical object in relation to the environment.

According to some embodiments of the invention, at least one of the obtaining, the slicing, the identifying, the applying, the associating, the superpositioning, and the outputting is performed by at least one computer.

Figure 4:
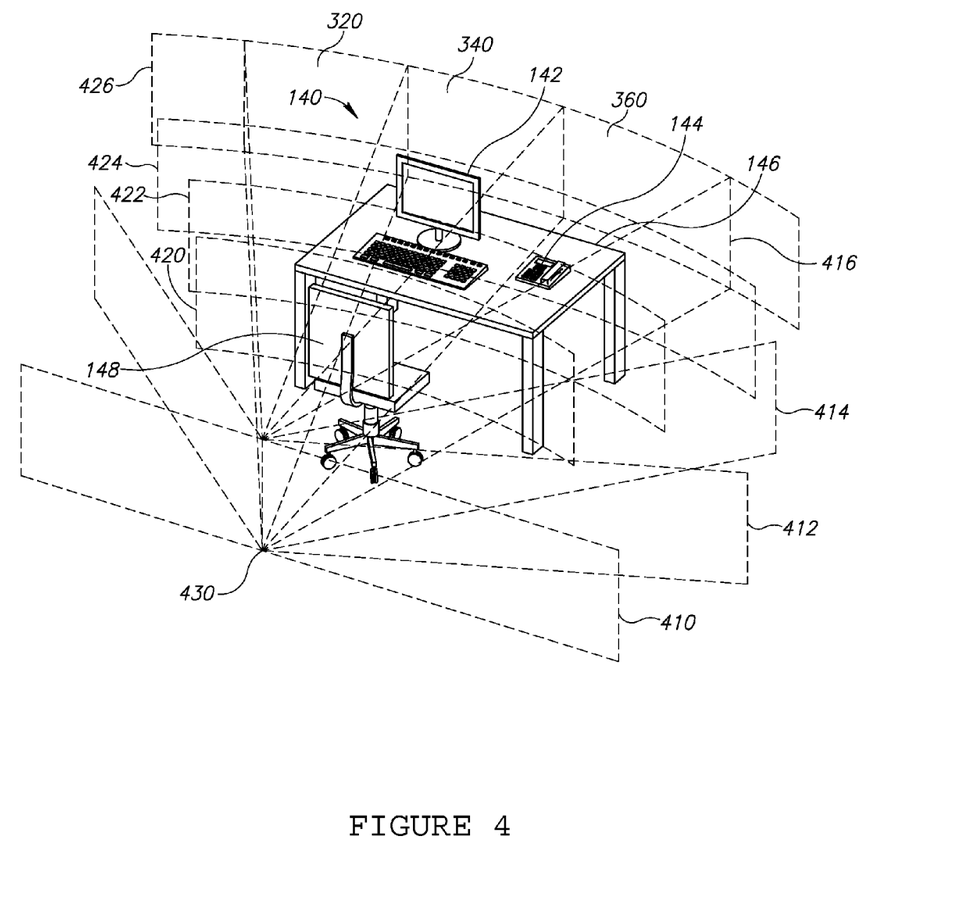
FIG. 4 is a model diagram illustrating an aspect according to some embodiments of the invention.

FIG. 4 is a model diagram obtained using, inter alia, imaging device 110 illustrating a further aspect according to some embodiments of the invention. The operation of a system similar in structure to the system illustrates in FIG. 1 will be explained below. The system includes an imaging device 110; a data processing module 100; and a user interface module (either 120 or 130, or both) wherein imaging device 110 being configured to obtain an image of environment 140 having a background and at least one physical object distinguishable from the background (such as desk 146, chair 148, computer screen 142, and phone 144).

Consistent with some embodiments of the invention, data processing module 100 is configured to: obtain using imaging device 110, a three-dimensional model of an environment containing at least one physical object; (ii) partition the three-dimensional model by surfaces (e.g., 410, 412, 414, and 416, being planes or 420, 422, 424, and 426, being spheres); (iii) identify, for each surface at a time, and surface by surface in a specified order, if at least a portion of the at least one physical object being cross-sectioned by the surface; (iv) apply, in the specified order, a conversion function to each identified cross-section of the at least one physical object for generating a sound or tactile object-dependent signal; (v) associate a sound or tactile location-dependent signal unique for each surface; (vi) superposition, in the specified order, each object-dependent signal with a respective location-dependent signal for creating a combined object-location signal; and (vii) output the combined object-location signal to a user via an interface, wherein the combined object-location signal being usable for a blind person to determine location and characteristics of the at least one physical object in relation to the environment.

Figure 5:
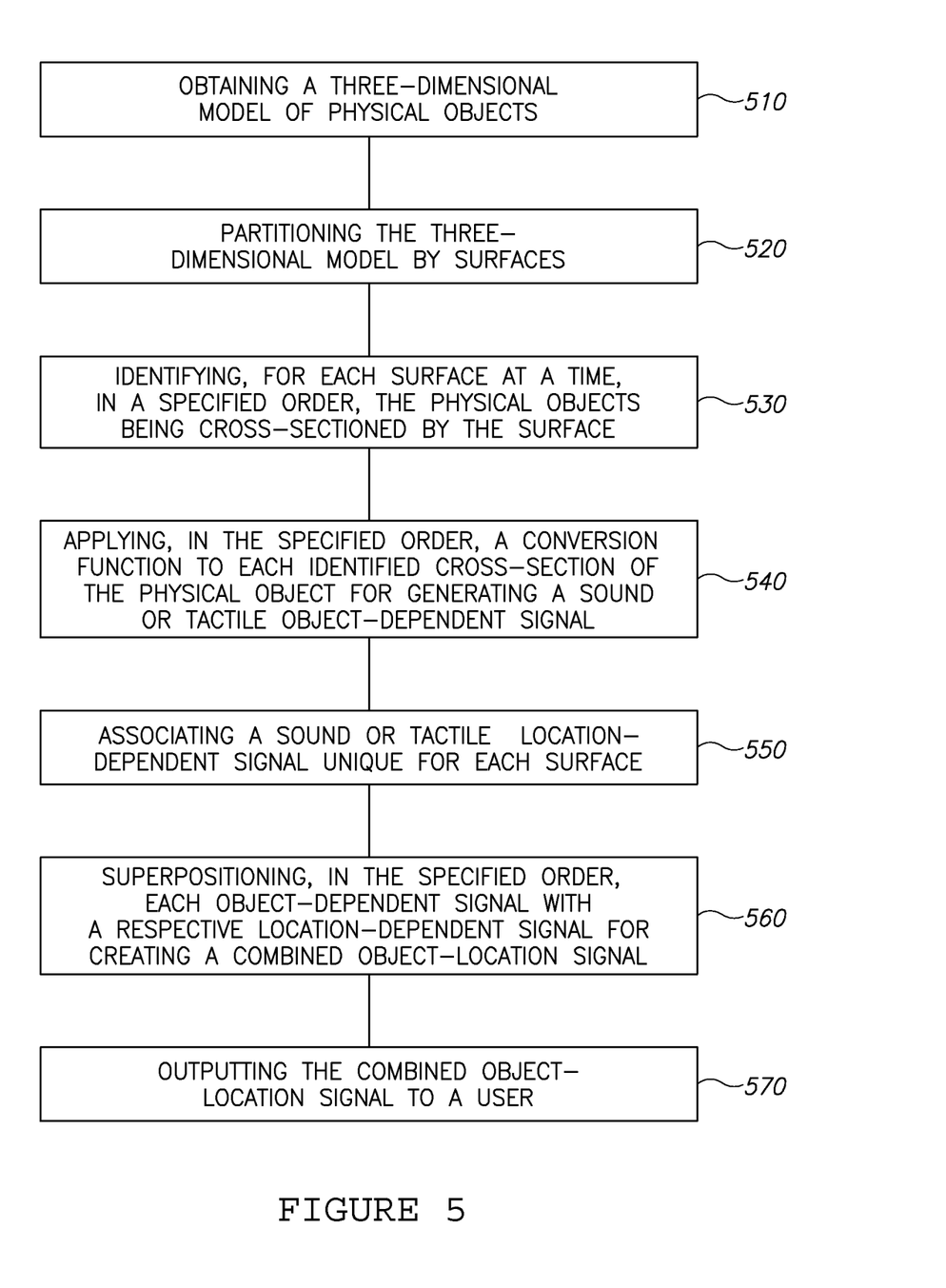
FIG. 5 is a high level flowchart illustrating a method according to some embodiments of the invention.

FIG. 5 is a high level flowchart illustrating a method according to some embodiments of the invention. The method includes: obtaining, using an imaging device, a three-dimensional model of an environment containing at least one physical object 510; partitioning the three-dimensional model by surfaces 520; identifying, for each surface at a time, and surface by surface in a specified order, if at least a portion of the at least one physical object being cross-sectioned by the surface 530; applying, in the specified order, a conversion function to each identified cross-section of the at least one physical object for generating a sound or tactile object-dependent signal 540; associating a sound or tactile location-dependent signal unique for each surface 550; superpositioning, in the specified order, each object-dependent signal with a respective location-dependent signal for creating a combined object-location signal 550; and outputting the combined object-location signal to a user via an interface, wherein the combined object-location signal being usable for a blind person to determine location and characteristics of the at least one physical object in relation to the environment 560.

According to some embodiments of the invention, at least one of the obtaining, the partitioning, the identifying, the applying, the associating, the superpositioning, and the outputting is performed by at least one computer.

According to some embodiments of the invention, each surface is an image that comprises an array of pixels, each pixel being associated with a location, a color and a brightness level, and wherein the conversion function maps the array of pixels into a temporal sound signal or two dimensional tactile signal in accordance with the location, the color and the brightness level of each pixel.

According to some embodiments of the invention the surfaces may be concentric spheres or concentric cylinders, and wherein the specified order may be either inbound or outbound of a specified center 430. Advantageously, this feature may enable the user to improve his or her distance conception of the objects in his or her environment.

According to some embodiments of the invention the surfaces may be radial planes going through a specified axis, defined by specified center 430, and wherein the specified order may be wither clockwise or counterclockwise around the axis.

According to some embodiments of the invention, the specified order is determined dynamically by the user so that the user can determined the spatial scan pattern of his or her environment.

Figure 6:
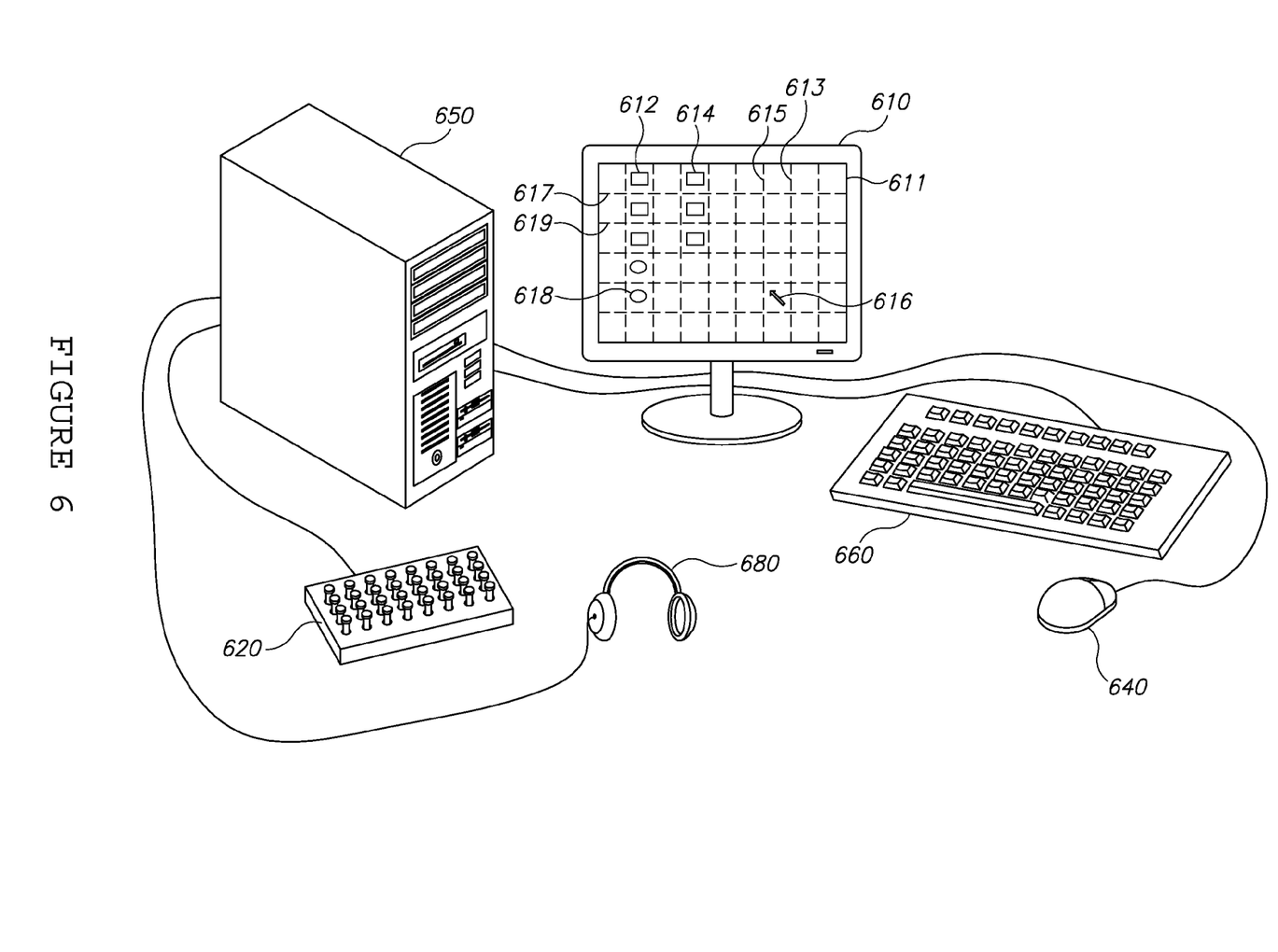
FIG. 6 is a high level schematic diagram illustrating a system according to some embodiments of the invention.

FIG. 6 is a high level schematic diagram illustrating a system according to some embodiments of the invention. The system includes a computer screen 610 showing a graphic display 611; a data processing module (not shown) within a personal computer 650, that may be implemented as a computer program; headphones 680; and a tactile user interface module 620.

Data processing module is configured to: slice the graphic display into a plurality of slices defined by rows such as 617 and 619 and columns such as 613 and 615, wherein the graphic display exhibits a plurality of icons 618, and other graphic objects 612 and 614 that are associated each with a specified appearance and a specified functionality; apply, for each slice, a conversion function to each icon contained within the slice, for generating a sound or tactile icon-dependent signal; associate a sound or tactile location-dependent signal unique for each slice; track a user-controlled (e.g. via 640) indicator 616 over the graphic display for detecting a location of indicator 616; superposition, over time, the location-dependent signal associated with the location of indicator 616 with all icon-dependent signals of the icons that are located within a specified range from indicator 616, for creating a combined icon-location signal; and output the combined icon-location signal to a user via the user interface, wherein the combined icon-location signal being usable for a blind person to determine location, appearance, functionality of icons on the graphic display.

According to some embodiments of the invention, the slice comprises pixels, each pixel being associated with a location, a color and a brightness level, and wherein the conversion function maps a two dimensional array of pixels into a temporal sound signal or two-dimensional tactile signal in accordance with the location, the color and the brightness level of each pixel and further in view of the functionality of the icon associated with the pixels.

Advantageously, The aforementioned combination of tactile and auditory input simultaneously yields a multi-sensory stimulation that can be most useful and may provide maximal behavior benefit when performance on each component in its own is limited, being exactly the situation when blind persons try to understand a visual image captured by a webcam using tactile and auditory inputs. The complementary approach of using tactile sensing together with auditory algorithms allows better learning and recognition and enhanced detection of motion and moving objects in addition to object recognition.

Figure 7:
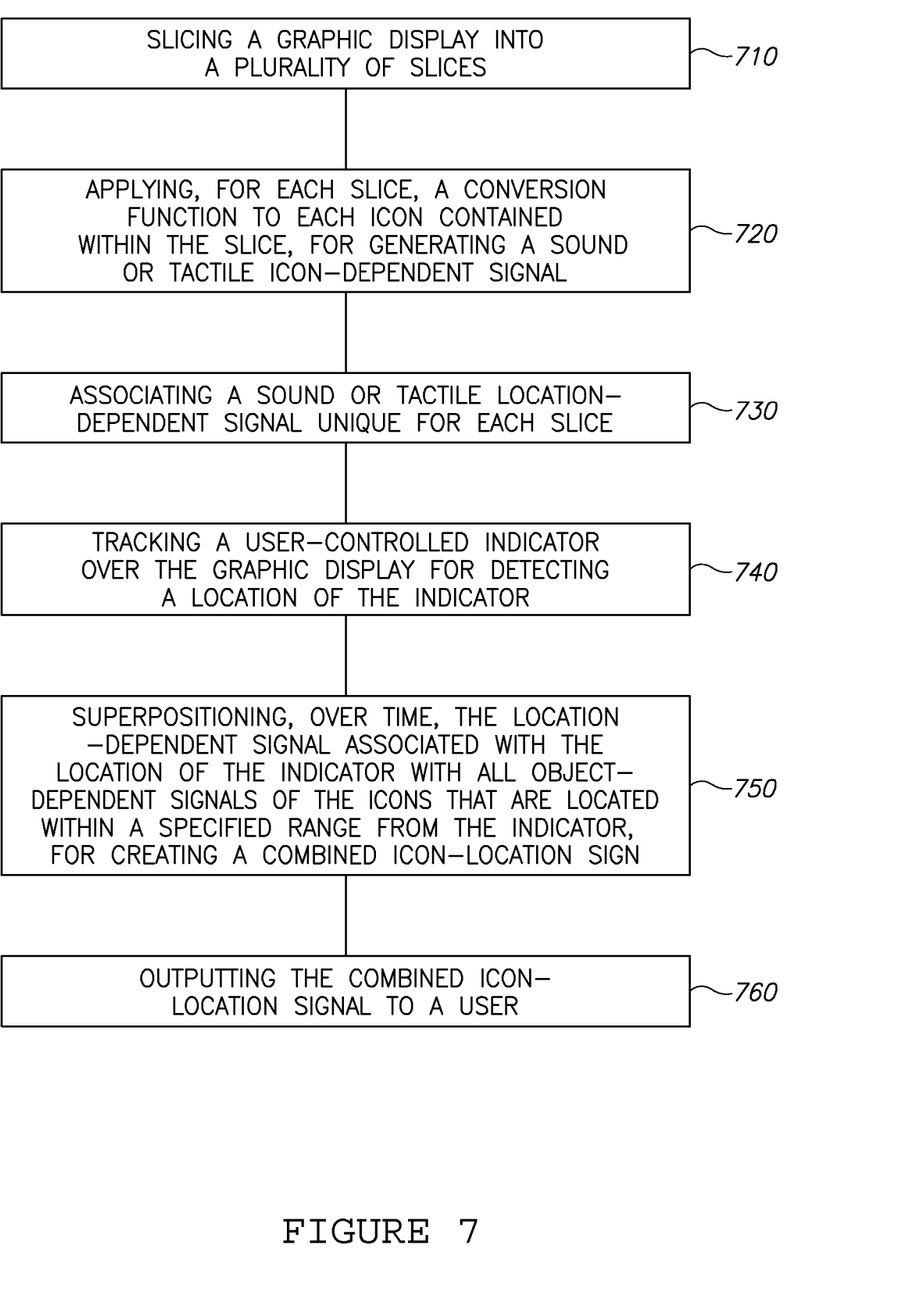
FIG. 7 is a high level flowchart illustrating a method according to some embodiments of the invention.

FIG. 7 is a high level flowchart illustrating a method according to some embodiments of the invention. The method includes: slicing a graphic display into a plurality of slices, wherein the graphic display exhibits a plurality of objects and icons that are associated each with a specified appearance and a specified functionality 710; applying, for each slice, a conversion function to each object or icon contained within the slice, for generating a sound or tactile object-dependent signal 720; associating a sound or tactile location-dependent signal unique for each slice 730; tracking a user-controlled indicator over the graphic display for detecting a location of the indicator 740; superpositioning, over time, the location-dependent signal associated with the location of the indicator with all object-dependent signals of the objects or icon that are located within a specified range from the indicator, for creating a combined object-location signal 750; and outputting the combined object-location signal to a user via an interface, such as headphones, wherein the combined object-location signal being usable for a blind person to determine location, appearance, functionality of objects and icons on the graphic display 760.

According to some embodiments of the invention, at least one of the obtaining, the slicing, the tracking, the applying, the associating, the superpositioning, and the outputting is performed by at least one computer.

According to some embodiments of the invention, the slice comprises an array of pixels, each pixel being associated with a location, a color and a brightness level, and wherein the conversion function maps a two dimensional array of pixels into a temporal sound signal or two-dimensional tactile signal in accordance with the location, the color and the brightness level of each pixel and further in view of the functionality of the icon associated with the pixels.

Advantageously, embodiments of the present invention are aimed primarily for the aid devices for the visually impaired. However, it is understood that the necessary modification may be performed on embodiments of the present invention in order to provide alternative vision for sighted person. For example, using an infrared imaging device in conjunction with an infrared illuminating source may provide military personnel with alternative means of orientation in vision-restricted environments or additional means to deliver information to pilots beyond visual input.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code embodied on a computer readable medium may be transmitted using any appropriate medium, including but not limited to wireless, wire-line, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like, conventional procedural programming languages, such as the "C" programming language or similar programming languages, as well as scripting languages such as Javascript and the like. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The aforementioned flowchart and diagrams illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element. \

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention may be implemented in the testing or practice with methods and materials equivalent or similar to those described herein.

Any publications, including patents, patent applications and articles, referenced or mentioned in this specification are herein incorporated in their entirety into the specification, to the same extent as if each individual publication was specifically and individually indicated to be incorporated herein. In addition, citation or identification of any reference in the description of some embodiments of the invention shall not be construed as an admission that such reference is available as prior art to the present invention.

What is claimed is:

1. A method comprising:
    capturing by an imaging device, an image from a scene having a background and at least one object distinguishable from the background;
    slicing said image into a plurality of slices, each being a surface within the time-space;
    repeatedly scanning the scene along a predefined scanning pattern by visiting adjacent slices, one by one, in a specified order;
    applying an image-to-sound conversion to each object visited along the scanning, so as to provide a sequence of auditory representations of objects in the scene, each auditory representation being indicative of characteristics of its representative object;
    adjusting the auditory representation of each one of the objects, based on its respective position within the time-space, so that same or similar objects positioned at different locations within the time space are auditory distinguishable from each other;
    applying an image-to-touch conversion to each object visited along the scanning, so as to provide a sequence of tactile representations of objects in the scene, each tactile representation being indicative of characteristics of its representative object; and
    combining the auditory and tactile representations so that auditory and tactile representations of the same object are presented to a human user simultaneously.

2. The method according to claim 1, wherein said image comprises an array of pixels, each pixel being associated with a location, a color and a brightness level, and wherein the image-to-sound conversion maps the array of pixels into a temporal sound signal and the image-to-tactile conversion maps the array of pixels into two dimensional tactile signal, in accordance with the location, the color and the brightness level of each pixel.

3. The method according to claim 1, wherein in case that the scene is two-dimensional, the slices are radial and the scanning path is circular.

4. The method according to claim 1, wherein the image-to-sound conversion comprises a mapping of objects into a set of sounds associated with real musical instruments, such that one or more musical instruments are used to represent, in one or more operational states, at least one of: shape, position, and color of each object.

5. The method according to claim 1, wherein in case that the scene is three-dimensional, the slices are spherical and the scanning path is directed from proximal to distal in regards with the human user.

6. The method according to claim 1, where the specified order is determined dynamically by the user.

7. A system comprising:
    (1) an imaging device configured to capture an image from a scene having a background and at least one object distinguishable from the background;
    (2) a data processing module configured to:
        (a) slice said image-into a plurality of slices, each being a surface within the time-space;
        (b) repeatedly scan the scene along a predefined scanning pattern by visiting adjacent slices, one by one, in a specified order;
        (c) apply an image-to-sound conversion to each object visited along the scanning, so as to provide a sequence of auditory representations of objects in the scene, each auditory representation being indicative of characteristics of its representative object;
        (d) adjust the auditory representation of each one of the objects, based on its respective position within the time-space, so that same or similar objects positioned at different locations within the time space are auditory distinguishable from each other;
        apply an image-to-touch conversion to each object visited along the scanning, so as to provide a sequence of tactile representations of objects in the scene, each tactile representation being indicative of characteristics of its representative object;
        and combine the auditory and tactile representations so that auditory and tactile representations of the same object are presented to a human user simultaneously; and
    (3) a user interface module configured to output the adjusted auditory representations and the tactile representations to the human user via an interface.

8. The system according to claim 7, wherein the image comprises an array of pixels, each pixel being associated with a location, a color and a brightness level, and wherein the image-to-sound conversion maps the array of pixels into a temporal sound signal and the image-to-touch conversion maps the array of pixels into two dimensional tactile signal in accordance with the location, the color and the brightness level of each pixel.

9. The system according to claim 7, wherein in case that the scene is two-dimensional, the slices are radial and the scanning path is circular.

10. The system according to claim 7, wherein the image-to-sound conversion comprises a mapping of objects into a set of sounds associated with real musical instruments, such that one or more musical instruments are used to represent, in one or more operational states, at least one of: shape, position, and color of each object.

11. The system according to claim 7, wherein in case that the scene is three-dimensional, the slices are spherical and the scanning path is directed from proximal to distal in regards with the human user.

12. The system according to claim 7, where the specified order is determined dynamically by the user.

13. A method comprising:
 slicing a graphic display into a plurality of slices, wherein the graphic display exhibits a plurality of objects and icons that are associated each with a specified appearance and a specified functionality;
 applying, for each slice, an image-to-sound conversion to each object or icon contained within the slice, so as to provide a sequence of auditory representations of objects and icons in the scene, each auditory representation being indicative of characteristics of its representative object;
 adjusting the auditory representation of each one of the objects or icons, based on its respective position in the scene, so that same or similar objects positioned at different locations are auditory distinguishable from each other;
 applying, for each slice, an image-to-touch conversion to each object or icon contained within the slice, so as to provide a sequence of tactile representations of objects or icons, each tactile representation being indicative of characteristics of its representative object or icon;
 tracking a user-controlled indicator over the graphic display for detecting a location of the indicator;
 superpositioning, over time, the location-dependent signal associated with the location of the indicator with all the auditory and tactile representations of objects or icons that are located within a specified range from the indicator, for creating a combined object location signal; and
 outputting the combined object-location signal to a human user via an interface, wherein the combined object-location signal being usable for a blind person to determine location, appearance, functionality of objects and icons on the graphic display, wherein the combined signal is generated so that both properties of the object and the location thereof are sensually distinguishable.

14. A system comprising:
 a graphic display;
 a data processing module; and
 a user interface module,
 wherein the data processing module is configured to:
  (1) slice the graphic display into a plurality of slices, wherein the graphic display exhibits a plurality of objects and icons that are associated each with a specified appearance and a specified functionality;
  (2) apply, for each slice, an image-to-sound conversion to each object or icon contained within the slice, so as so as to provide a sequence of auditory representations of objects and icons in the scene, each auditory representation being indicative of characteristics of its representative object;
  (3) adjust the auditory representation of each one of the objects or icons, based on its respective position in the scene, so that same or similar objects positioned at different locations are auditory distinguishable from each other;
  (4) apply, for each slice, an image-to-touch conversion to each object or icon contained within the slice, so as to provide a sequence of tactile representations of objects or icons, each tactile representation being indicative of characteristics of its representative object or icon;
  (5) track a user-controlled indicator over the graphic display for detecting a location of the indicator;
  (6) superposition, over time, the location-dependent signal associated with the location of the indicator with all the auditory and tactile representations of objects or icons that are located within a specified range from the indicator, for creating a combined object-location signal, wherein the combined signal is generated so that both properties of the icon and the location thereof are sensually distinguishable; and
  (7) output the combined icon-location signal to a human user via the user interface, wherein the combined icon-location signal being usable for a blind person to determine location, appearance, functionality of icons on the graphic display.

15. A computer program product, the computer program product comprising:
 computer readable non-transitory storage medium having computer readable program code embodied therewith, the computer readable program code comprising:
 computer readable program code configured to obtaining an image from a scene having a background and at least one object distinguishable from the background;
 computer readable program code configured to slice said image a plurality of slices, each being a surface within the time-space;
 computer readable program code configured to repeatedly scan the scene along a predefined scanning pattern by visiting adjacent slices, one by one, in a specified order;
 computer readable program code configured to apply an image-to-sound conversion to each object visited along the scanning, so as to provide a sequence of auditory representations of objects in the scene, each auditory representation being indicative of characteristics of its representative object;
 computer readable program code configured to adjust the auditory representation of each one of the objects, based on its respective position within the time-space, so that same or similar objects positioned at different locations within the time space are auditory distinguishable from each other;
 computer readable program code configured to apply an image-to-touch conversion to each object visited along the scanning, so as to provide a sequence of tactile representations of objects in the scene, each tactile representation being indicative of characteristics of its representative object;
 computer readable program code configured to combine the auditory and tactile representations so that auditory and tactile representations of the same object are presented to a human user simultaneously; and,
 computer readable program code configured to present the sequence of adjusted auditory and the tactile representations to a human user.

16. The computer program product according to claim 15, wherein said image comprises an array of pixels, each pixel being associated with a location, a color and a brightness level, and wherein the image-to-sound conversion maps the array of pixels into a temporal sound signal and the image-to-touch conversion maps the array of pixels into two-dimensional tactile signal in accordance with the location, the color and the brightness level of each pixel.

\* \* \* \* \*